(12) United States Patent
Fausett et al.

(10) Patent No.: US 10,478,600 B2
(45) Date of Patent: Nov. 19, 2019

(54) SEGMENTAL CRIMPER HAVING INDIVIDUALLY HEATED CRIMPER SEGMENTS AND METHOD OF USING THE SAME

(71) Applicant: Machine Solutions, Inc., Flagstaff, AZ (US)

(72) Inventors: Kevin Brent Fausett, Tucson, AZ (US); Tulsie P. Sumeer, Tucson, AZ (US); Caitlyn McErlane Henderson, Tucson, AZ (US); Joseph Gregory Augustine, Denver, CO (US); Thomas J. Motsenbocker, Flagstaff, AZ (US); Daniel Kasprzyk, Flagstaff, AZ (US); Jake W. Davis, Flagstaff, AZ (US)

(73) Assignee: MACHINE SOLUTIONS, INC., Pittsburgh, PA (US)

( * ) Notice: Subject to any disclaimer, the term of this patent is extended or adjusted under 35 U.S.C. 154(b) by 992 days.

(21) Appl. No.: 14/288,783

(22) Filed: May 28, 2014

(65) Prior Publication Data

US 2015/0343184 A1  Dec. 3, 2015

(51) Int. Cl.

| | | |
|---|---|---|
| *A61M 25/10* | (2013.01) | |
| *B32B 37/00* | (2006.01) | |
| *B32B 37/06* | (2006.01) | |
| *B32B 37/14* | (2006.01) | |
| *B32B 38/00* | (2006.01) | |
| *B29C 65/00* | (2006.01) | |
| *B29C 65/18* | (2006.01) | |
| *B29C 65/38* | (2006.01) | |
| *B25B 27/10* | (2006.01) | |
| *B29L 31/00* | (2006.01) | |

(52) U.S. Cl.
CPC ..... *A61M 25/1034* (2013.01); *B32B 37/0046* (2013.01); *B32B 37/06* (2013.01); *B32B 37/142* (2013.01); *B32B 38/0012* (2013.01); *A61M 25/104* (2013.01); *A61M 2207/00* (2013.01); *A61M 2207/10* (2013.01); *Y10T 156/1005* (2015.01)

(58) Field of Classification Search
CPC .. A61M 25/1038; A61M 25/1034; B21J 9/08; B29C 66/81463; B29C 66/81414; B29C 66/81415; B29C 65/04
See application file for complete search history.

(56) References Cited

U.S. PATENT DOCUMENTS

| | | |
|---|---|---|
| 5,360,330 A | 11/1994 | Jensen et al. |
| 5,370,618 A | 12/1994 | Leonhardt |

(Continued)

*Primary Examiner* — Jacob T Minskey
*Assistant Examiner* — Marta S Dulko
(74) *Attorney, Agent, or Firm* — Thompson Coburn LLP

(57) ABSTRACT

A segmental crimper comprises at least three crimper segments and an actuator. The crimper segments are arranged circumferentially about a crimper axis that defines axial and radial directions. The crimper segments are movable relative to each other in a manner such that the crimper segments collectively define a variable size aperture that is aligned with the crimper axis. Each of the crimper segments comprises a radio frequency heating element. The actuator is operatively connected to the crimper segments in a manner such that movement of the actuator causes all of the crimper segments to simultaneously move relative to each other and alters the size of the aperture.

7 Claims, 4 Drawing Sheets

(56) References Cited

U.S. PATENT DOCUMENTS

| | | | |
|---|---|---|---|
| 5,423,754 | A | 6/1995 | Cornelius et al. |
| 6,056,906 | A | 5/2000 | Werneth et al. |
| 6,858,083 | B2 * | 2/2005 | Sterud ................... B29C 65/18 156/378 |
| 7,069,794 | B2 | 7/2006 | Motsenbocker et al. |
| 7,438,548 | B2 | 10/2008 | Augustine et al. |
| 7,744,805 | B2 | 6/2010 | Augustine et al. |
| 7,762,804 | B1 | 7/2010 | Stupecky |
| 7,892,201 | B1 | 2/2011 | Laguna et al. |
| 2001/0001890 | A1 | 5/2001 | Austin |
| 2002/0138966 | A1 | 10/2002 | Motsenbocker |
| 2002/0163104 | A1 * | 11/2002 | Motsenbocker .. A61M 25/1002 264/320 |
| 2004/0135281 | A1 * | 7/2004 | Eidenschink ..... A61M 25/1038 264/69 |
| 2005/0188525 | A1 | 9/2005 | Weber et al. |
| 2007/0114701 | A1 | 5/2007 | Stenzel |
| 2008/0086084 | A1 | 4/2008 | Schaeffer et al. |
| 2009/0299452 | A1 | 12/2009 | Eidenschink et al. |
| 2014/0008007 | A1 | 1/2014 | Wang et al. |

\* cited by examiner

SEGMENTAL CRIMPER HAVING INDIVIDUALLY HEATED CRIMPER SEGMENTS AND METHOD OF USING THE SAME

CROSS-REFERENCE TO RELATED APPLICATIONS

Not Applicable.

STATEMENT REGARDING FEDERALLY SPONSORED RESEARCH OR DEVELOPMENT

Not Applicable.

APPENDIX

Not Applicable.

BACKGROUND OF THE INVENTION

Field of the Invention

The present invention pertains to devices and methods for bonding angioplasty balloons on catheters. More particularly, the present invention pertains to a segmental crimping device that comprises a radio frequency (RF) heating element in each of its segments. By crimping the cuff of the angioplasty balloon radially inward against a catheter and thereafter activating the heating elements, the cuff can be thermally bonded to the catheter.

General Background

There are several common techniques used to secure angioplasty balloon cuffs to catheters. One technique involves the use of hot jaw clamps and PTFE or FEP heat shrink material. Another similar method uses hot air and PTFE or FEP heat shrink material. Still another method involves the use of lasers and PTFE or FEP heat shrink material. All of these methods utilize heat shrink material placed over the balloon cuff to provide the hoop tension necessary to form an acceptable and annularly contiguous annular thermal bond between the balloon cuff and catheter. As can be appreciated, the heat shrink material must also conduct the heat necessary to melt the balloon cuff. When using hot jaws, the heat begins to transfer less effectively as the heat shrink pulls away from the jaws. This is problematic in that it causes variation in bond strength as a result. In the case of hot air, it is inherently difficult to maintain thermal control and it is often difficult to properly and consistently aim the hot air flow. Moreover, changes in ambient conditions can result in changes in bond properties. In the case of laser bonding, the heat is generated when the laser is absorbed by the catheter. The catheter then transfers the heat radially outward into the balloon cuff. That is problematic in that the absorption rate is impacted by the pigment, surface texture, and/or reflectivity of the catheter, which may vary from one catheter to the next. Moreover, relying on heat shrink material to generate the hoop tension necessary to form an acceptable bond is inherently problematic given that the properties of the heat shrink material often varies from batch to batch and the hoop tension generated is impacted by temperature exposure.

In view of the foregoing, prior art techniques of bonding angioplasty balloon cuffs to catheters have drawbacks.

SUMMARY OF THE INVENTION

The present invention overcomes many difficulties associated with thermal bonding angioplasty balloon cuffs to catheters. Rather than use of heat shrink material, the present invention involves using a segmental crimper to annularly compress a balloon cuff against a catheter. The crimper segments then heat and melt the balloon cuff to the catheter. That being said, although heat shrink material is not required, it could still be used in combination with the invention for bonding angioplasty balloon cuffs to catheters. Moreover, as discussed in the Detailed Description below, the invention is also applicable to circumferentially bonding other types of thermoplastic tubes or rods to each other.

In one aspect of the invention, a segmental crimper comprises at least three crimper segments and an actuator. The at least three crimper segments are arranged circumferentially about a crimper axis that defines axial and radial directions. The crimper segments are movable relative to each other in a manner such that the crimper segments collectively define a variable size aperture that is aligned with the crimper axis. Each of the crimper segments comprises a radio frequency heating element. The actuator is operatively connected to the crimper segments in a manner such that movement of the actuator causes all of the crimper segments to simultaneously move relative to each other and alters the size of the aperture.

Another aspect of the invention pertains to a method of bonding an angioplasty balloon to a catheter. The method comprises creating an assembly that includes a catheter and an angioplasty balloon cuff. The assembly is created by inserting the catheter coaxially into the angioplasty balloon cuff. The angioplasty balloon cuff has opposite open ends and a respective end margin adjacent to each of the opposite ends. The insertion occurs in a manner such that the catheter extends through the angioplasty balloon cuff and axially out of the opposite ends of the angioplasty balloon cuff. The method then further comprises inserting a portion of the assembly into an aperture of a segmental crimper. The segmental crimper comprises at least three crimper segments arranged circumferentially about a crimper axis and an actuator. The crimper axis defines axial and radial directions. The aperture is aligned with the crimper axis and defined by the crimper segments. The crimper segments are movable relative to each other via the actuator in a manner such that the aperture is variable in radial size. Each of the crimper segments comprises a radio frequency heating element. The actuator operatively connects the crimper segments in a manner such that movement of the actuator causes all of the crimper segments to simultaneously move relative to each other and alter the size of the aperture. The method then still further comprises actuating the actuator in a manner reducing the radial size of the aperture of the segmental crimper such that the crimper segments radially press at least one of the end margins of the angioplasty balloon cuff inward against the catheter. Finally, the method thereafter comprises activating the radio frequency heating elements of the crimper segments while the at least one of the end margins of the angioplasty balloon cuff is pressed radially inward against the catheter. The activation of the heating elements causes portions of the crimper segments to increase in temperature to at least a degree such that the at least one of the end margins of the angioplasty balloon cuff becomes circumferentially thermal bonded to the catheter.

Further features and advantages of the present invention, as well as the operation of the invention, are described in detail below with reference to the accompanying drawings.

Figure 1:
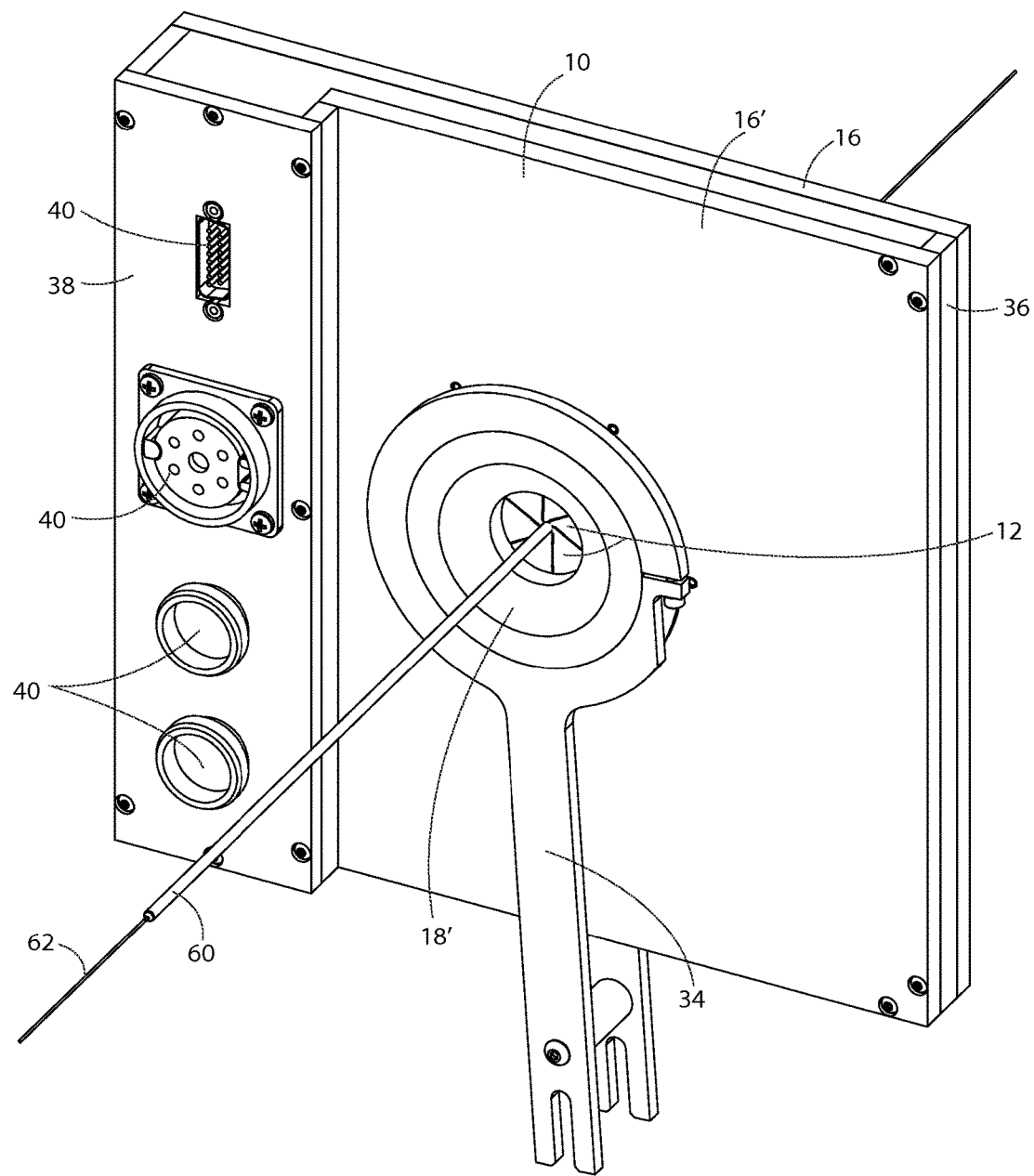
FIG. 1 depicts a step in accordance with the invention wherein a segmental crimper is crimping an angioplasty balloon cuff to a catheter during a step of thermal bonding the cuff to a catheter.
Figure 2:
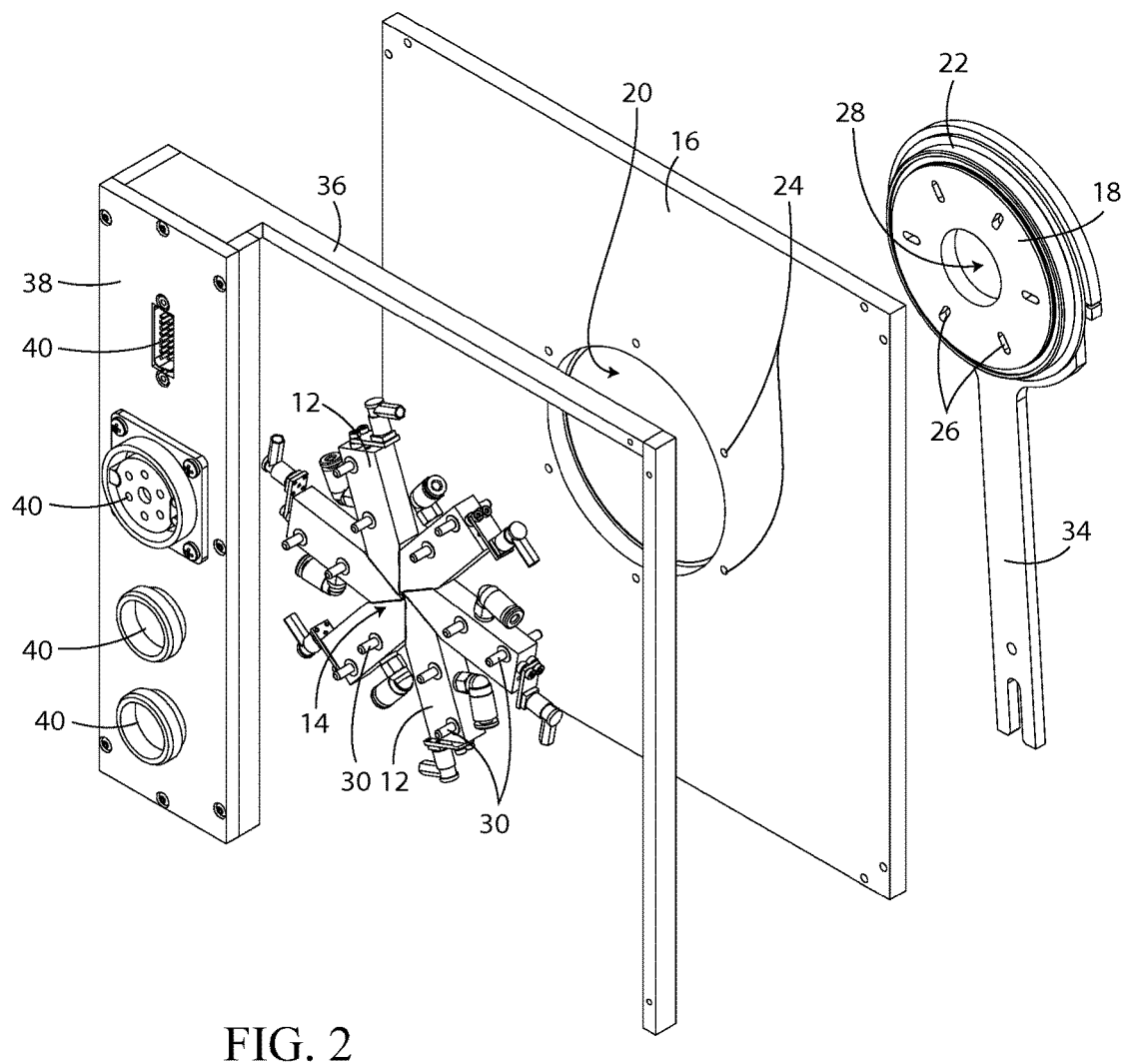
FIG. 2 depicts a partial exploded view of the segmental crimper shown in FIG. 1.
Figure 3:
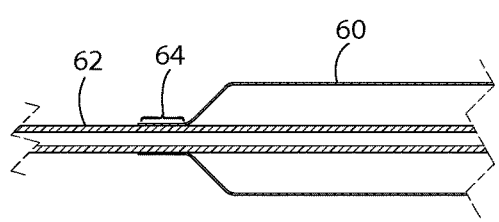
FIG. 3 depicts a detailed cross-sectional view of an angioplasty balloon cuff that has been thermal bonded to a catheter.

Reference numerals in the written specification and in the drawing figures indicate corresponding items.

DETAILED DESCRIPTION

As mentioned above, rather than using heat shrink material, the present invention involves using a segmental crimper to annularly compress a balloon cuff against a catheter. In general, segmental crimpers comprise at least three crimper segments that slideably contact each other and collectively define an aperture. By sliding and rotating all of the segments relative to each other, the aperture diameter can be adjusted, thereby allowing the crimper segments to radially compress items. Various know methods exist for moving the crimper segments relative to each other, each of which could be employed to practice the present invention.

An embodiment of the invention is depicted in the drawing figures. The invention preferably uses a segmental crimper (10) that comprises six or more crimper segments (12). The crimper segments (12) are circumferentially arranged about an axis and define an aperture (14) that is aligned with the axis. The crimper segments (12) are movable relative to each other and are supported and guided by a set of first and second mounting members (16, 18). More preferably, the crimper segments (12) are supported and guided by a second set of mounting members (16', 18') that are substantially a mirror image of the first set of mounting members. For simplicity, the details and operation of only the first set of mounting members (16, 18) are described herein.

The first mounting member (16) comprises a circular opening (20) and is configured to be stationary. The second mounting member (18) is disc shaped and is pivotally mounted within the circular opening (20) of the first mounting member (16) via a bearing (22). The first mounting member (16) comprises a plurality of small holes (24), as many as there are crimper segments (12), spaced circumferentially about the larger circular opening (20). The second mounting member (18) comprises an equal number of radial slots (26) spaced circumferentially about a central opening (28) that extends through the second mounting member. A pair of pins (30) connects each crimper segment (12) to the first and second mounting members (16, 18). The pins protrude axially from the crimper segments (12). One of the pins (30) is configured and adapted to engage with one of the small holes (24) of the first mounting member (16) and the other is configured to engage with one of the slots (26) of the second mounting member (18). As such, each crimper segment (12) is pivotally attached to a respective one of the small holes (24) of the first mounting member (16) and is configured to pivot about that small hole and radially slide relative to the second mounting member (18) when, and only when, the second mounting member pivots within the circular opening (20) of the first mounting member. Thus, pivotal movement of the second mounting member (18) causes the tip portions (32) of the crimper segments (12) to collectively move closer to or farther from the crimper axis and thereby controls the size of the aperture (14).

The segmental crimper (10) also preferably comprises an actuator (34). As shown, the actuator (34) is preferably a lever arm that is secured to the second mounting member (18) for rotating the second mounting member relative to the first mounting member (16). However, it should be appreciated that the actuator (34) could be any type of device, such as gears, links, cables, etc., that is configured to control the pivotal movement of the second mounting member (18) relative to the first mounting member (16). Regardless, the actuator (34) is preferably electronically controlled and is preferably electronically powered.

Still further, the segmental crimper (10) preferably comprises a frame (36) and an interface housing (38). The frame preferably has a thickness approximately equal to that of the crimper segments (12) and is configured to connect the first mounting members (16, 16') to each other with the crimper segments 12 therebetween. The interface housing (38) comprises a plurality of electrical connectors (40) and is configured to house electrical circuitry (not shown) for supplying electricity to the crimper segments (12).

Figures 4, 5:
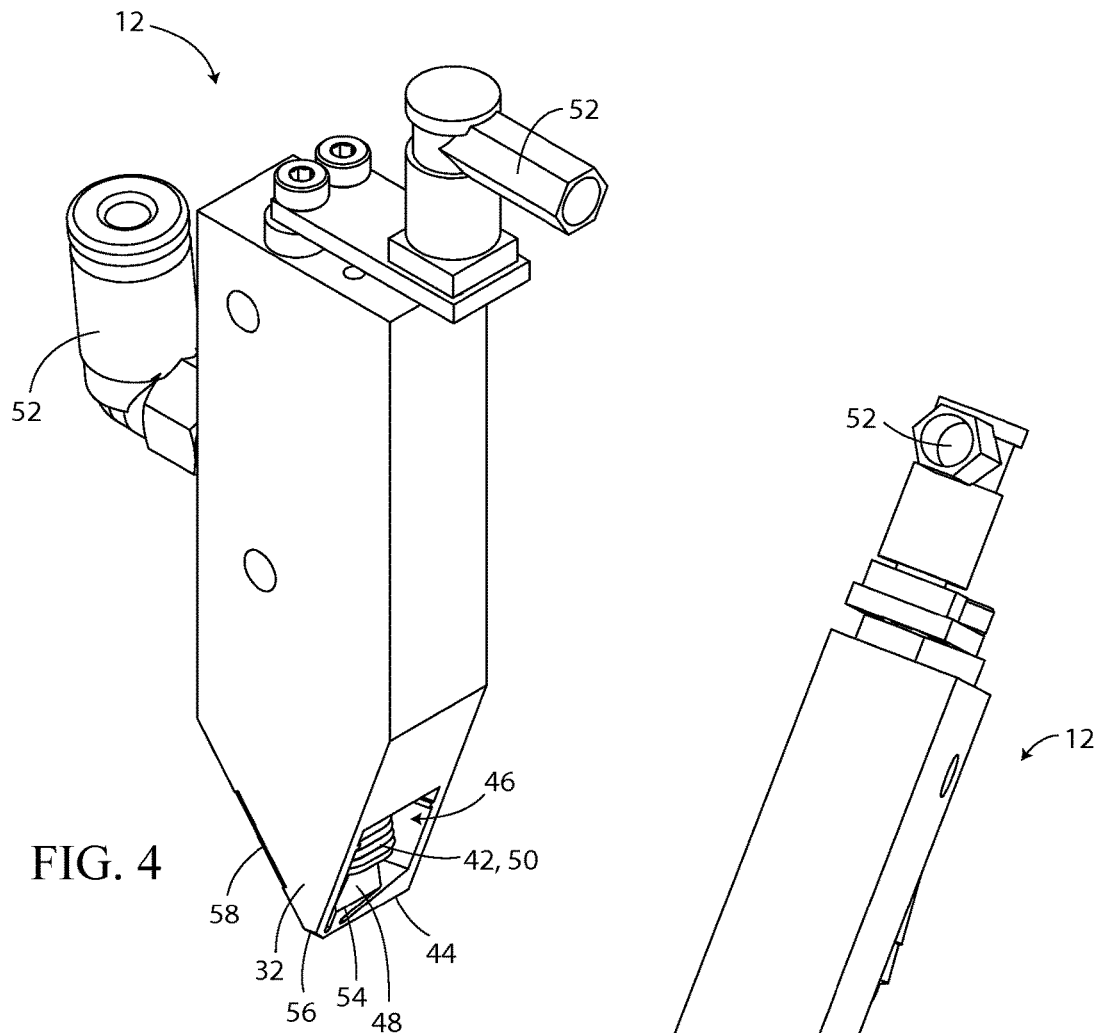
FIG. 4 depicts a crimper segment of the segmental crimper shown in FIG. 1.
FIG. 5 depicts the crimper segment in a different orientation.
Figure 6:
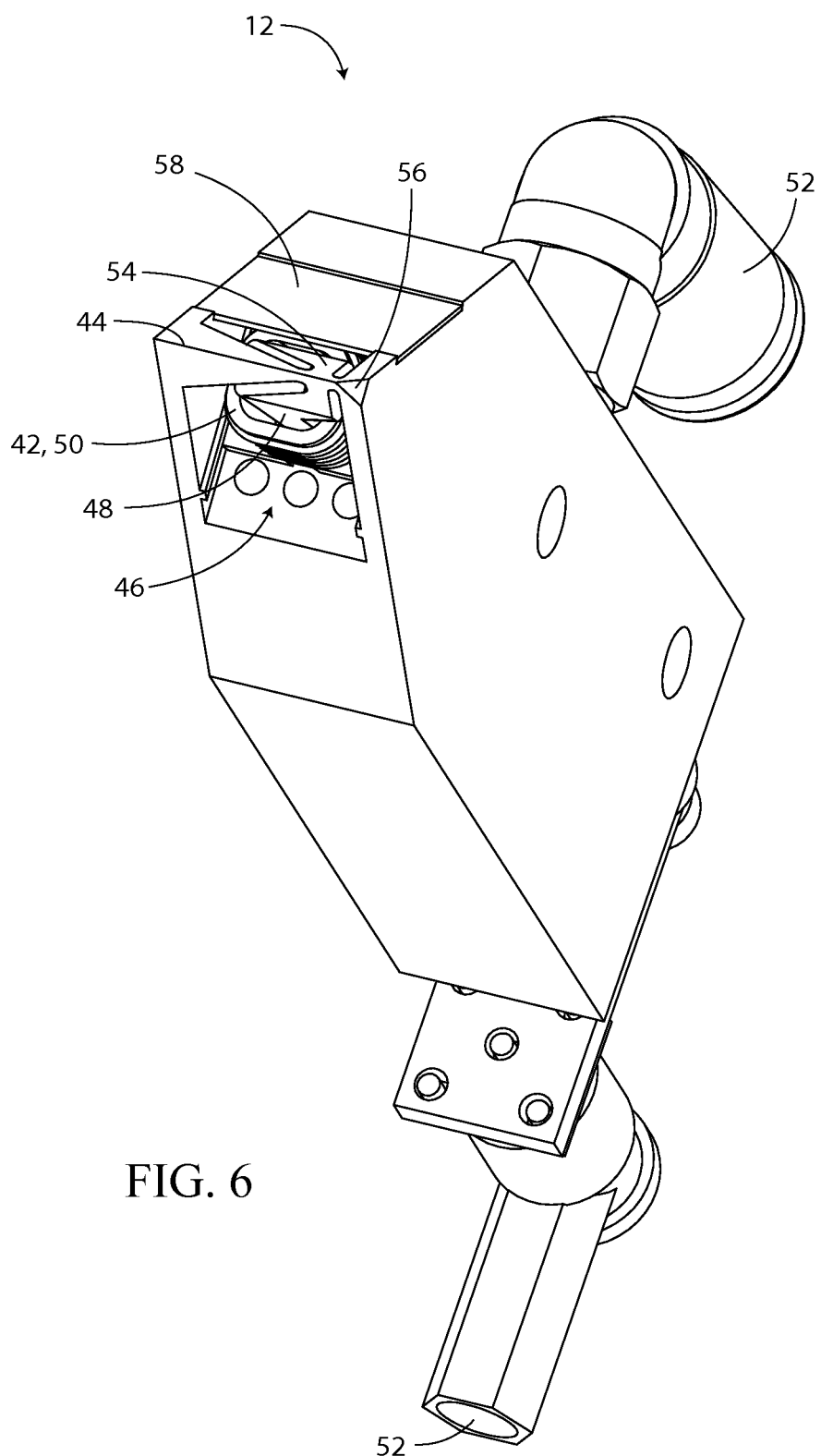
FIG. 6 depicts the crimper segment in yet another orientation.

FIGS. 4-6 show one of the crimper segments (12) by itself (the other crimper segments being identical thereto). The crimper segment (12) comprises an RF heating element (42) located in the tip portion (32) of the crimper segment. Preferably the RF heating element (42) is positioned in a cavity (46) of the crimper segment 12 as close as possible to the axially oriented edge (44) of the tip portion (32). More specifically, the tip portion (32) of the crimper segment (12) comprises a metallic bridge portion (48) that extends radially within and across the cavity (46) from the axially oriented edge portion (44) of the crimper segment. The RF heating element (42) of the crimper segment (12) comprises a coil (50) of electrically conductive wire that encircles the bridge portion (48). The coil (50) is operatively connected to interface housing (38) of the segmental crimper (10) via flexible electrical wires (not shown) that extend out of electrical ports (52) of the crimper segment (12). Although the majority of bridge portion (48) of the crimper segment (12) is axially centered in the crimper segment, it also preferably comprises a jog portion (54) adjacent to the axially oriented edge (44) of the crimper segment. As such, heat generated by the coil (50) heats the axially oriented edge (44) of the crimper segment (12) non-centrally. Preferably, the crimper segment (12) also comprises a small chamfer (56) adjacent to the jog portion (54) such that heat generated by the coil (50) heats the axially oriented edge (44) of the crimper segment from as close to the axial end of the axially oriented edge as possible. Still further, the crimper segment (12) preferably comprises a shield piece (58) that covers one side of the crimper segment's cavity (46). The shield piece (58) helps prevent heat and magnetic flux from being transferred between adjacent crimper segments (12).

In use, an unbonded angioplasty balloon cuff (60) is slid over a catheter (62) and a mandrel (not shown) is inserted into the catheter. That assembly is then partially inserted into the aperture (14) of the segmental crimper (10), from the axial side of the crimper segments (12) having the chamfers (56) in manner such that only an end margin (64) of the balloon cuff (60) extends between the crimper segments (12). The actuator (34) is then actuated to decrease the size of the aperture (14), thereby radially compressing the end margin (64) of the balloon cuff (60) against the catheter (62). With the end margin (64) of the balloon cuff (60) compressed against the catheter, the heating elements (42) of the crimper segments (12) are activated. This causes the tip portions (32) of the crimper segments (12) adjacent to their axially oriented edges (44) to rapidly heat and melt and bond the end margin (64) of the balloon cuff (60) to the catheter (62). Almost immediately upon melting the end margin (64) of the balloon cuff (60) to the catheter (62), the heating elements (42) are deactivated. As such, heat in the crimper segments (12) adjacent to their axially oriented edges (44) rapidly dissipates to other portions of the crimper segments (12) and drops below the melting temperature of the balloon cuff (60). That then cools and solidifies the bonded portion of balloon cuff (60), after which the actuator (34) is triggered to enlarge the aperture (14) of the segmental crimper (10) to release the balloon/catheter assembly from the segmental crimper.

Although the segmented crimper was developed primarily to bond angioplasty balloon cuffs to catheters, it should be appreciated that the segmental crimper of the invention could also be used to bond any annular thermal plastic device around a cylindrical object or to bond equal diameter thermal plastic tubes or rods to each other end-to-end. Furthermore, although the segmental crimper of the invention is capable of bonding balloon cuffs to catheters without the use of heat shrink material, heat shrink cuffs could still be used in conjunction with the invention to prevent flashing or sticking. Mold release material could also be used to prevent sticking.

In view of the foregoing, it should be appreciated that the invention has several advantages over the prior art. For example, using the invention, thermal bonds can be formed rapidly and with consistency. The segmental crimper also provides constant contact with the balloon cuff during the heating step (for thermal conductivity), supplies consistent hoop force during the bonding process, and allows tight control over the diameter of the bonded material.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

It should also be understood that when introducing elements of the present invention in the claims or in the above description of exemplary embodiments of the invention, the terms "comprising," "including," and "having" are intended to be open-ended and mean that there may be additional elements other than the listed elements. Additionally, the term "portion" should be construed as meaning some or all of the item or element that it qualifies. Moreover, use of identifiers such as first, second, and third should not be construed in a manner imposing any relative position or time sequence between limitations. Still further, the order in which the steps of any method claim that follows are presented should not be construed in a manner limiting the order in which such steps must be performed, unless such and order is inherent.

What is claimed is:

1. A segmental crimper comprising:
   at least three crimper segments arranged circumferentially about a crimper axis, the crimper axis defining axial and radial directions, the crimper segments being movable relative to each other in a manner such that the crimper segments collectively define a variable size, circular bounded aperture that is aligned with the crimper axis, each of the crimper segments comprising a radio frequency heating element including a coil of electrically conductive wire; and
   an actuator being operatively connected to the crimper segments in a manner such that movement of the actuator causes all of the crimper segments to simultaneously move relative to each other and alters the size of the aperture.

2. A segmental crimper in accordance with claim 1 wherein the coil and a majority of the bridge portion of each of the crimper segments is centrally positioned axially between the opposite end faces and a minority of the bridge portion skews toward one of the opposite end faces as it approaches the edge of the respective crimper segment.

3. A segmental crimper in accordance with claim 1 wherein the segmental crimper comprises first and second mounting members that are pivotally connected to each other about the crimper axis, each of the crimper segments is pivotally connected to the first mounting member about a respective pivot axis, each of the crimper segments is connected to the second mounting member in a manner such that the respective crimper segment is able to pivot relative to the second mounting member and radially slideable relative to the second mounting member, and the actuator is configured to control the pivotal movement of the first and second mounting members relative to each other.

4. A segmental crimper in accordance with claim 3 wherein the segmental crimper comprises a frame, the first mounting member is configured and adapted to be stationary relative to the frame, the actuator is fixed relative to the second mounting member and is configured to pivot the second mounting member relative to the frame.

5. A segmental crimper in accordance with claim 1 wherein the actuator is adapted and configured to move the segments between an open position and a radially reduced position, wherein in the open position, the segments define the circular, bounded aperture with a first diameter sufficiently large to allow first and second objects to be inserted therethrough with the first object coaxially arranged about the second object, and wherein in the radially reduced position, the segments define the circular, bounded aperture with a diameter smaller than the first diameter wherein the segments press the first object against the second object.

6. A segmental crimper in accordance with claim 5 wherein the actuator is adapted and configured to move the segments from the open position to the radially reduced position with consistent force against the first object when heating.

7. A segmental crimper in accordance with claim 5 wherein the actuator is adapted and configured to move the segments from the open position to the radially reduced position with constant contact against the first object when heating.

* * * * *